(12) United States Patent
Huang (10) Patent No.: US 7,759,839 B2
(45) Date of Patent: Jul. 20, 2010

(54) ACOUSTIC DECOUPLING IN CMUTS

(75) Inventor: Yongli Huang, San Jose, CA (US)

(73) Assignee: Kolo Technologies, Inc., San Jose, CA (US)

( * ) Notice: Subject to any disclaimer, the term of this patent is extended or adjusted under 35 U.S.C. 154(b) by 682 days.

(21) Appl. No.: 11/696,652

(22) Filed: Apr. 4, 2007

(65) Prior Publication Data

US 2007/0228878 A1    Oct. 4, 2007

Related U.S. Application Data

(60) Provisional application No. 60/744,242, filed on Apr. 4, 2006.

(51) Int. Cl.
*H02N 1/00* (2006.01)
*H04R 31/00* (2006.01)
*G01H 11/00* (2006.01)

(52) U.S. Cl. .............................. 310/309; 73/649; 29/594
(58) Field of Classification Search ................. 310/307, 310/334, 309; 29/594; 73/649
See application file for complete search history.

(56) References Cited

U.S. PATENT DOCUMENTS

| 6,669,644 B2 | 12/2003 | Miller |
| 6,837,110 B2 | 1/2005 | Miller |
| 2003/0028106 A1 | 2/2003 | Miller |
| 2003/0114760 A1 | 6/2003 | Robinson |
| 2004/0160144 A1* | 8/2004 | Daft et al. ..................... 310/334 |
| 2005/0075571 A1 | 4/2005 | Barnes |
| 2005/0177045 A1* | 8/2005 | Degertekin et al. ......... 600/457 |
| 2005/0200242 A1* | 9/2005 | Degertekin ................. 310/334 |
| 2006/0075818 A1* | 4/2006 | Huang et al. ................. 73/649 |
| 2007/0013266 A1* | 1/2007 | Chang et al. ................ 310/311 |
| 2007/0013269 A1* | 1/2007 | Huang ......................... 310/334 |
| 2007/0180916 A1* | 8/2007 | Tian et al. ..................... 73/649 |
| 2008/0290756 A1* | 11/2008 | Huang ......................... 310/300 |
| 2009/0126183 A1* | 5/2009 | Chang et al. .................. 29/594 |

OTHER PUBLICATIONS

Jin et al, "Characterization of One-Dimensional Capacitive Micromachined Ultrasonic Immersion Transducer Arrays," IEEE Transactions on Ultrasonics, Ferroelectrics, and Frequency Control, vol. 48, No. 3, May 2001, pp. 750-760.

Roh et al, "Finite Element Analysis of Underwater Capacitor Micromachined Ultrasonic Transducers," IEEE Transactions on Ultrasonics, Ferroelectrics, and Frequency Control, vol. 49, No. 3, Mar. 2002, pp. 293-298.

* cited by examiner

*Primary Examiner*—Thomas M Dougherty
(74) *Attorney, Agent, or Firm*—Lee & Hayes, PLLC (57) ABSTRACT

A capacitive micromachined ultrasonic transducer (cMUT) has an acoustic decoupling feature. A cavity is introduced underneath the regular cMUT element, preferably in the substrate, to provide acoustic decoupling. Trenches are also introduced to separate the cMUT elements and to provide further acoustic decoupling. The acoustic decoupling feature may be used in both conventional membrane-based cMUT and the newer embedded-spring cMUT (ESCMUT). Exemplary fabrication methods are also described.

22 Claims, 7 Drawing Sheets

ACOUSTIC DECOUPLING IN CMUTS

PRIORITY

This application claims priority from U.S. Provisional Applications Ser. No. 60/744,242, filed Apr. 4, 2006.

This application further incorporates herein by reference in entirety the following:

International Application (PCT) No. PCT/IB2006/051567, entitled "METHODS FOR FABRICATING MICRO-ELECTRO-MECHANICAL DEVICES", filed on May 18, 2006;

International Application (PCT) No. PCT/IB2006/051568, entitled "MICRO-ELECTRO-MECHANICAL TRANSDUCERS", filed on May 18, 2006; and International Application (PCT) No. PCT/IB2006/051569, entitled "MICRO-ELECTRO-MECHANICAL TRANSDUCERS", filed on May 18, 2006.

BACKGROUND OF THE INVENTION

Capacitive micromachined ultrasonic transducers (cMUTs) are electrostatic actuator/transducers, which are widely used in various applications. Ultrasonic transducers can operate in a variety of media including liquids, solids and gas. These transducers are commonly used for medical imaging for diagnostics and therapy, biochemical imaging, non-destructive evaluation of materials, sonar, communication, proximity sensors, gas flow measurements, in-situ process monitoring, acoustic microscopy, underwater sensing and imaging, and many others. In addition to discrete ultrasound transducers, ultrasound transducer arrays containing multiple transducers have been also developed. For example, two-dimensional arrays of ultrasound transducers are developed for imaging applications.

Compared to the widely used piezoelectric (PZT) ultrasound transducer, the MUT has advantages in device fabrication method, bandwidth and operation temperature. For example, making arrays of conventional PZT transducers involves dicing and connecting individual piezoelectric elements. This process is fraught with difficulties and high expenses, not to mention the large input impedance mismatch problem presented by such elements to transmit/receiving electronics. In comparison, the micromachining techniques used in fabricating MUTs are much more capable in making such arrays. In terms of performance, the MUT demonstrates a dynamic performance comparable to that of PZT transducers. For these reasons, the MUT is becoming an attractive alternative to the piezoelectric (PZT) ultrasound transducers.

The basic structure of a cMUT is a parallel plate capacitor with a rigid bottom electrode and a top electrode residing on or within a flexible membrane, which is used to transmit (TX) or detect (RX) an acoustic wave in an adjacent medium. A DC bias voltage is applied between the electrodes to deflect the membrane to an optimum position for cMUT operation, usually with the goal of maximizing sensitivity and bandwidth. During transmission an AC signal is applied to the transducer. The alternating electrostatic force between the top electrode and the bottom electrode actuates the membrane in order to deliver acoustic energy into the medium surrounding the cMUT. During reception the impinging acoustic wave vibrates the membrane, thus altering the capacitance between the two electrodes. An electronic circuit detects this capacitance change.

Figure 1:
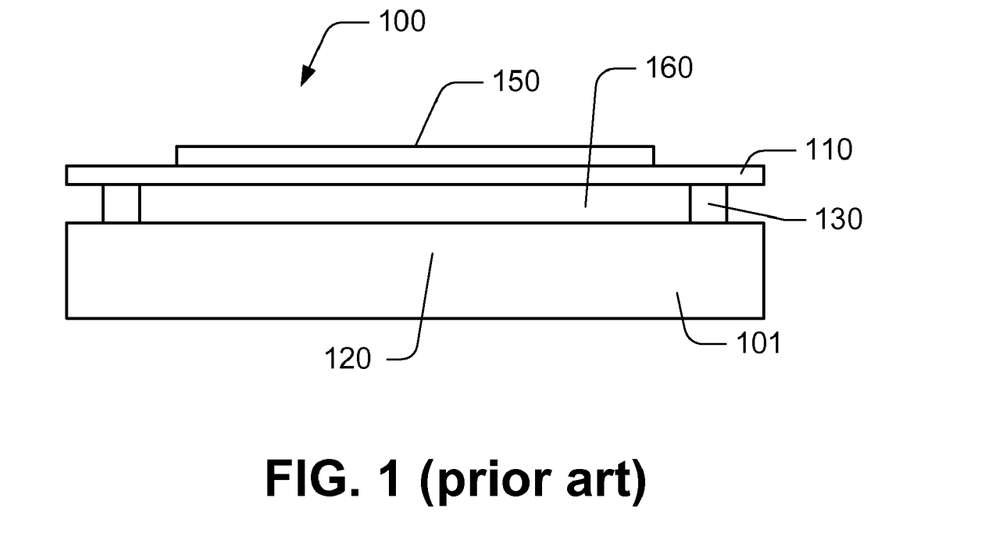
FIG. 1 is a schematic cross-sectional view of a conventional flexible membrane cMUT.

Two representative types of cMUT structures are conventional flexible membrane cMUT and the newer embedded-spring cMUT (ESCMUT). FIG. 1 shows a schematic cross-sectional view of a conventional flexible membrane cMUT 10, which has a fixed substrate 101 having a bottom electrode 120, a flexible membrane 110 connected to the substrate 101 through membrane supports 130, and a movable top electrode 150. The flexible membrane 110 is spaced from the bottom electrode 120 by the membrane supports 130 to form a transducing space 160.

Figure 2:
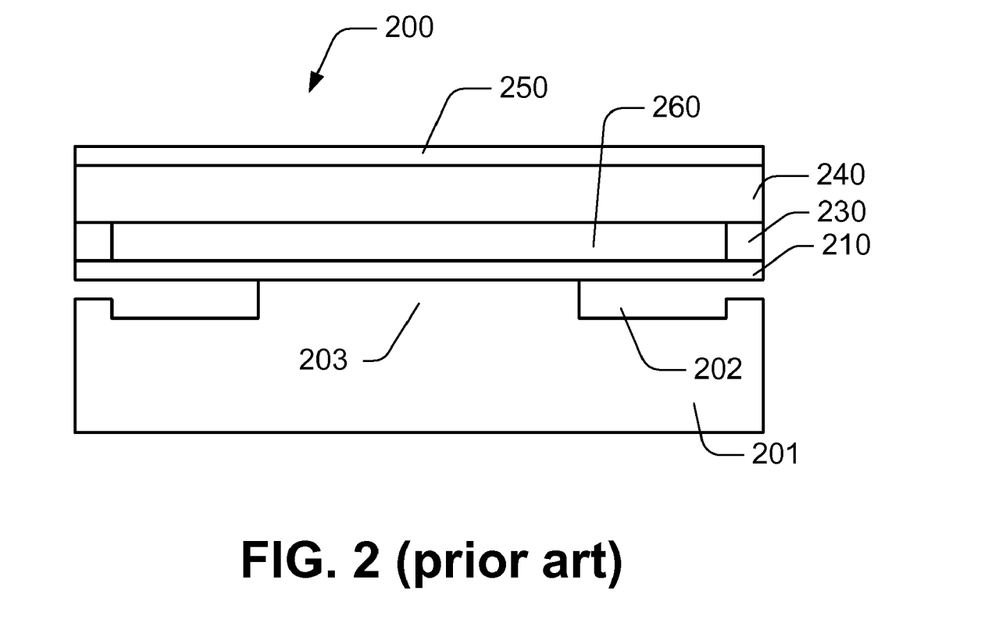
FIG. 2 is a schematic cross-sectional view of embedded-spring cMUT (ESCMUT).

FIG. 2 is a schematic cross-sectional view of embedded-spring cMUT (ESCMUT) 200, which is described in the PCT International Application No. PCT/IB2006/051568, entitled MICRO-ELECTRO-MECHANICAL TRANSDUCERS, filed on May 18, 2006; and International Application (PCT) No. PCT/IB2006/051569, entitled MICRO-ELECTRO-MECHANICAL TRANSDUCERS, filed on May 18, 2006, particularly the cMUTs shown in FIGS. 5A-5D therein. The cMUT 200 has a substrate 201, on top of which is a spring anchor 203 supporting a spring layer 210; a surface plate 240 connected to the spring layer 210 through spring-plate connectors 230; and a top electrode 250 connected to the surface plate 240. The cMUT 200 may be only a portion of a complete cMUT element (not shown). Usually multiple cMUTs (cMUT elements) are used as an array device.

In addition to emitting into an intended medium, the acoustic energy may also leak into substrate. There are at least two different sources for this leakage. One is the acoustic energy from the moving components of the cMUT coupling into the substrate through anchors, and another is the electrostatic force directly applied on the substrate. The acoustic energy coupling into the substrate may introduce cross-talking between cMUT elements and an acoustic ring between the two surfaces of the cMUT substrate. There is therefore a need to minimize the effect of the acoustic energy leaking into the substrate.

SUMMARY OF THE INVENTION

This application discloses acoustic decoupling features in the substrate to minimize the impact on the cMUT performance by the leaking of acoustic energy in the substrate. A cavity is introduced underneath the regular cMUT element to provide acoustic decoupling. Either a single cavity or multiple smaller cavities may be used for each cMUT element. The cavities may contain a vacuum or filled with a suitable material that is compatible with or has potential to improve acoustic decoupling.

In some embodiments, trenches are also introduced to separate the cMUT elements and to provide further acoustic decoupling. The trenches may reach deep down into the substrate to reach or even pass the cavity to improve acoustic decoupling performance.

The acoustic decoupling feature may be used in both conventional membrane-based cMUT and the newer embedded-spring cMUT (ESCMUT). Exemplary fabrication methods are also described.

BRIEF DESCRIPTION OF THE DRAWINGS

FIG. 6 shows a method to fabricate the acoustic decoupling features with cMUT elements.

FIG. 8 shows an exemplary fabrication method to add embedded cavities and trenches in the substrate of a conventional cMUT array.

FIG. 9 shows an exemplary fabrication method to add embedded cavities and trenches in the substrate of an ESCMUT array.

DETAILED DESCRIPTION

The acoustic decoupling feature in cMUT will be described in detail along with the figures, in which like parts are denoted with like reference numerals or letters. The new method may be used with a variety of transducers including capacitive micromachined ultrasonic transducers (MUT).

This disclosure describes acoustic decoupling features in the cMUT substrate to minimize the impact on the cMUT performance by the leakage of acoustic energy into the substrate. The acoustic decoupling features are introduced to address the issue of leaking acoustic energy in the substrate which may not only affect the performance of each cMUT element but also introduces the cross-talking between cMUT elements.

Figure 3:
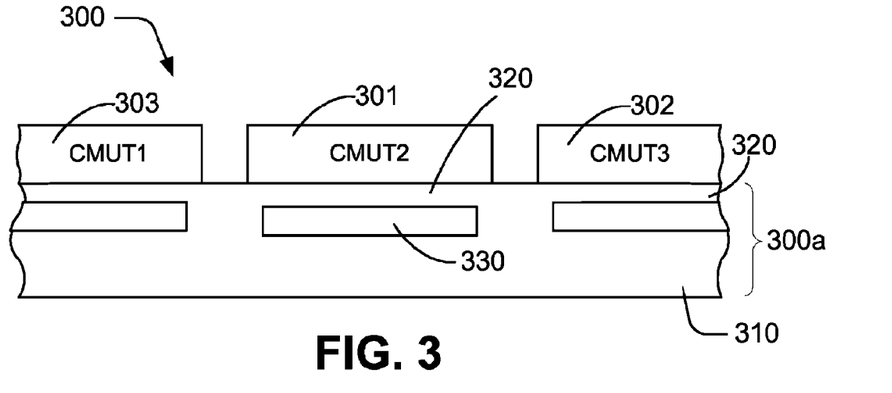
FIG. 3 shows a cMUT array having a basic decoupling feature.

FIG. 3 shows a cMUT array having a basic decoupling feature. The cMUT array 300 includes multiple cMUT elements 301, 302 and 303, all built on a cMUT base 300a that includes a lower base portion including the substrate 310, and an upper base portion including layer 320. The decoupling feature is a cavity 330 added into substrate 310 to control the acoustic rings in the substrate 310, as well as the acoustic coupling between cMUT elements 301, 302 and 303. The cavity 330 is generally placed under the layer 320 which acts both as a cover to the cavity 330 and a support to the rest of each cMUT element 301, 302 and 303. Multiple cavities 330 are embedded in the substrate 310, with each cavity placed directly under each cMUT element 320, 321 or 322 to minimize the acoustic energy leaking into the bulk part of the substrate 310. Alternatively, multiple smaller cavities similar to cavity 330 may be placed under each cMUT element. The cavity 330 may have any suitable size and shape placed at desired location in the substrate 310. The cavity 330 may contain a vacuum or filled with a suitable material that is compatible with or has potential to improve acoustic decoupling.

The depth of the cavity is defined by the thickness of the layer 350 above the cavity. The thickness of the layer 350 may be designed to be thin enough to push the frequency of acoustic ring in the layer 350 out of the cMUT operating frequency range.

Figure 4:
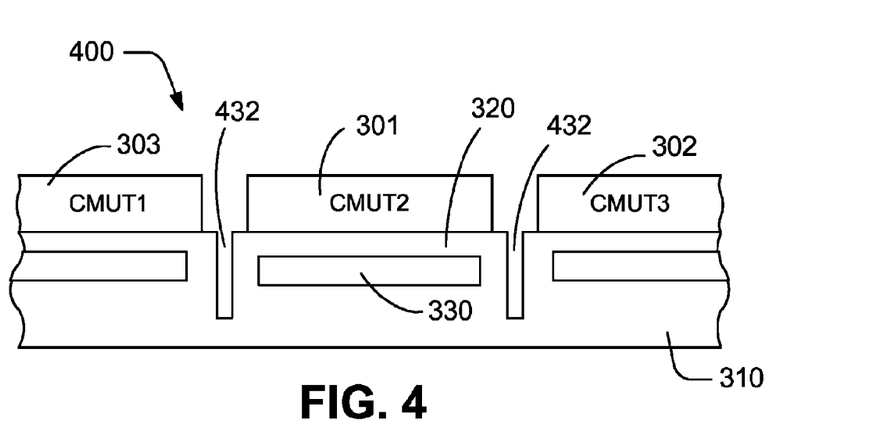
FIG. 4 shows a cMUT array having additional acoustic decoupling features.

FIG. 4 shows a cMUT array having additional acoustic decoupling features. The cMUT array 400 is based on the cMUT array 300 with added trenches 432 that cut through at least a part of the layer 320, and preferably cuts through the entire layer 320 and partially into the substrate 310. The additional trenches 432 may further control the cross-coupling between cMUT elements 301, 302 and 303 through the substrate 310. Trenches 432 may be etched between the cMUT elements 301, 302 and 303 to reach a partial death of the cavity 330, and may even reach beyond the entire depth of the cavity 330.

Figure 5:
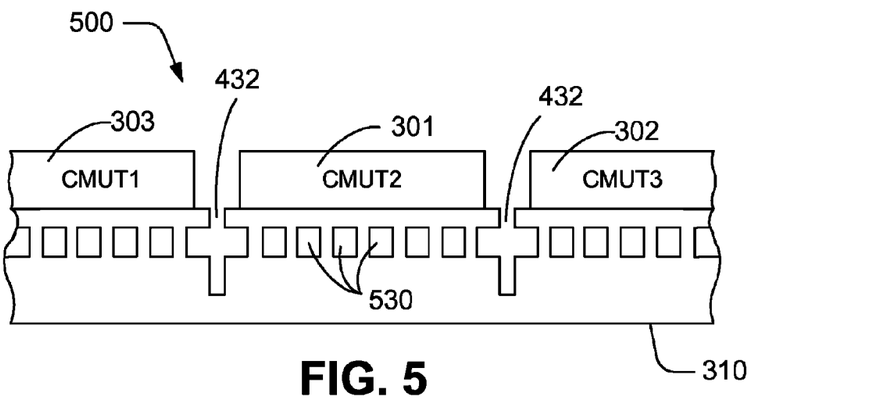
FIG. 5 shows a modification of the cMUT array of FIG. 4.

FIG. 5 shows a modification of the cMUT array of FIG. 4. The cMUT 500 is similar to that of the cMUT 400 except with a different cavity pattern. As shown, multiple cavities 530 are formed underneath each cMUT element 301, 302 and 303. The cavities 530 may be designed to have any suitable shapes and are distributed with various distribution patterns to achieve desired acoustic properties.

The acoustic decoupling features described herein may be applied in any suitable cMUT structure, including both conventional membrane-based cMUT as shown in FIG. 1 and newer embedded-spring cMUT (ESCMUT) as shown in FIG. 2.

FIG. 6 shows a method to fabricate the acoustic decoupling features with cMUT elements.

Figure 61:
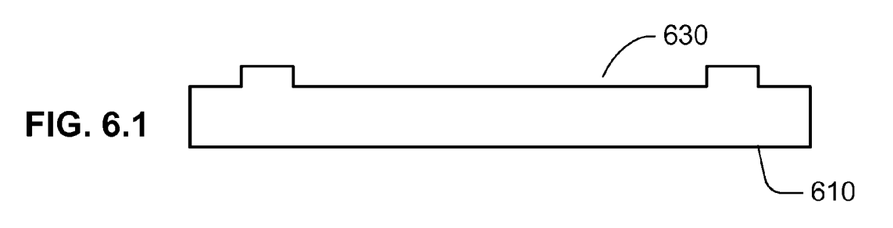

At step 1 (FIG. 6.1), a cavity pattern 630 is formed on wafer 610 by any etching method.

Figure 62:
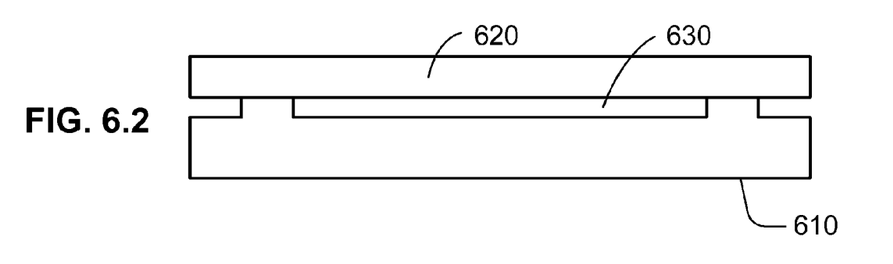

At step 2 (FIG. 6.2), a second wafer is bonded on the wafer 610 patterned in the first step. The second wafer may be grounded and polished to the desired thickness to form layer 620 placed above the cavity 630. The layer 620 may be a device layer made from a SOI wafer. Preferably, the top surface of the layer 620 has characteristics similar to that of a surface of a prime layer suited for device fabrication in the subsequent steps.

Figure 63:
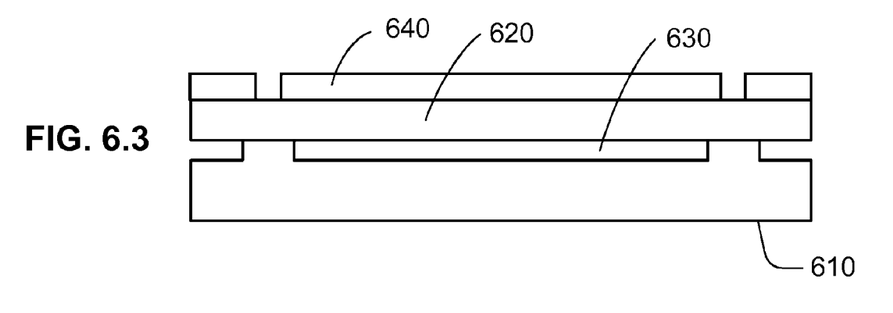

At step 3 (FIG. 6.3), a cMUT structure 640 is fabricated on top of the layer 620. In general, any kind of cMUT structure 640 that can be normally built on a prime wafer substrate may be built on the layer 620 to complete the cMUT fabrication. The cMUT structure 640 may be fabricated by surface micromachining technology, wafer bonding technology or any combination of these technologies.

Figure 64:
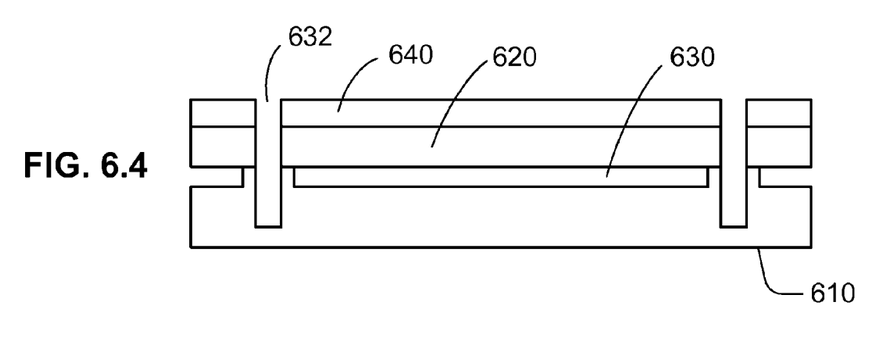
Figure 81:
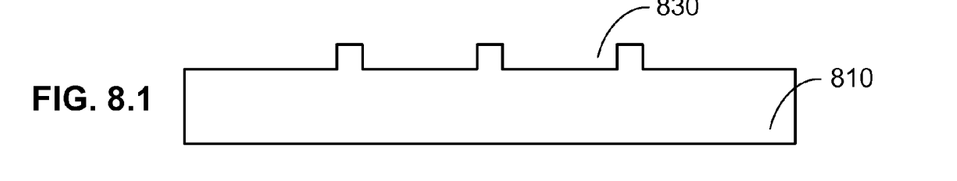
Figure 82:
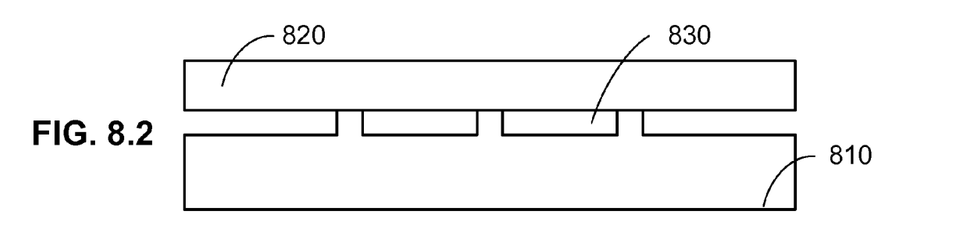

At step 4 (FIG. 6.4), trenches 632 are etched between cMUT elements to separate individual cMUT elements, and to further improve decoupling performance. In general, for the purpose of separating individual cMUT elements only, trenches 632 may only need to cut through the cMUT layer 620. However, trenches 632 may cut through layer 620, and may further cut through the wafer (substrate) 610 to reach the depth of the embedded cavities 630, or further beyond.

Figure 7:
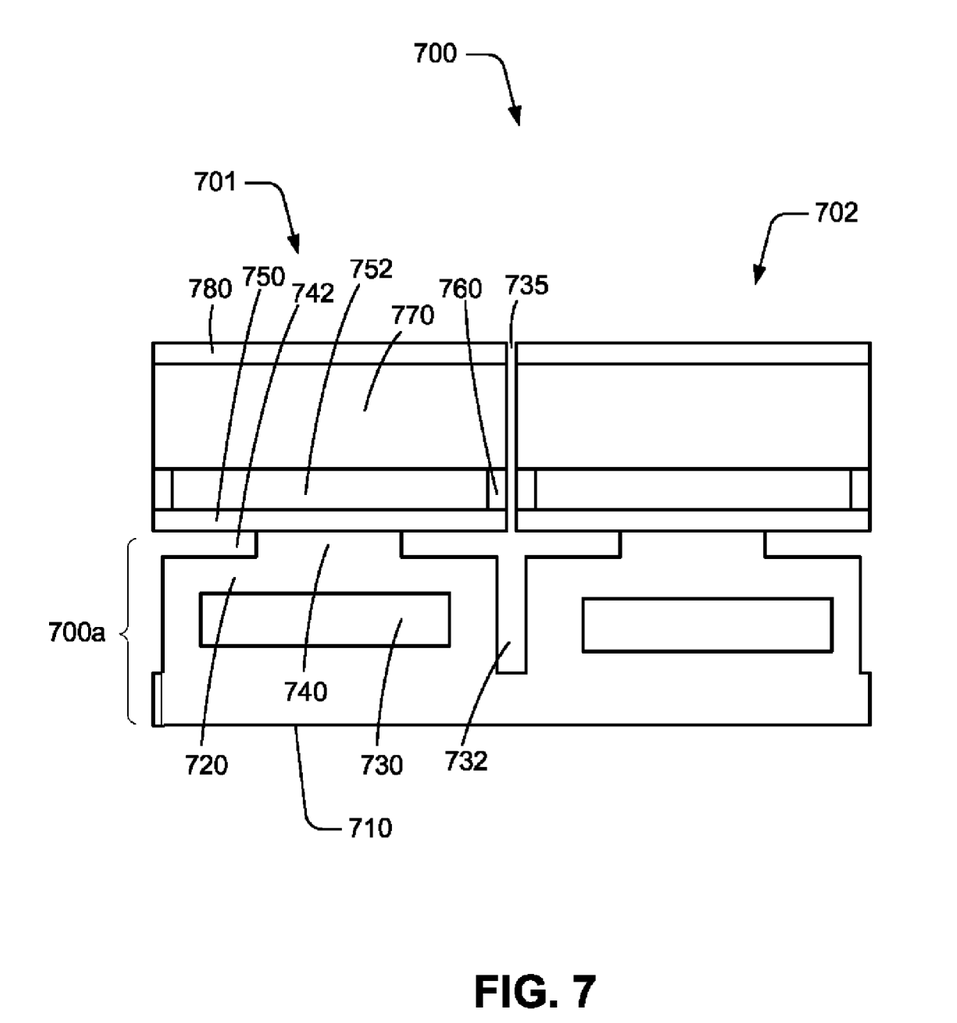
FIG. 7 shows an embedded-spring cMUT (ESCMUT) with embedded cavities for acoustic decoupling.

FIG. 7 shows an embedded-spring cMUT (ESCMUT) with embedded cavities for acoustic decoupling. The cMUT 700 is a part of a cMUT array containing multiple cMUT elements. FIG. 7 shows only two such cMUT elements 701 and 702 separated by a trench 735. The structure of the cMUT 700 is described by illustrating only one cMUT element 701, as each cMUT element may have similar or the same structure.

The cMUT element 701 can generally be viewed as a capacitor built on a base 700a. The base 700a includes a lower base portion which includes a part of substrate 710, and an upper base portion which includes layer 720. Cavity 730 is formed between substrate 710 and layer 720. A spring layer 750 is disposed above the upper base portion and anchored by spring anchor 740 connected to the layer 720 of the upper base portion. The spring anchor 740 spaces the spring layer 750 from the layer 720 of the upper base portion to form a cantilever-like structure having an anchored portion and a movable portion. The anchored portion of the spring layer 750 is fixed to the spring anchor 740 but is not required to cover the top of the spring anchor 740 completely. The movable portion of the spring layer 750 is suspended from the layer 720 to form the cantilever.

A surface plate 770 is disposed above the spring layer 750 and supported by spring-plate connectors 760 which are connected to the movable portion of the spring layer 750. The spring-plate connectors 760 space the surface plate 770 from the spring layer 750 to define a transducing space 752. The surface plate 770 includes a top electrode 780, which may either be a separate layer or an integral part of the surface plate 770 if the surface plate 770 is made of a conductive material. To make a functional cMUT, a variable capacitor is formed between the top electrode 780 and a bottom electrode, which may be served by any of the spring layer 750, the spring anchor 740 and the layer 720, or a conductive layer attached thereto. In one embodiment, for example, the spring layer 750 further has a separate conductive layer (not shown) attached thereto to act as the bottom electrode. Alternatively, the spring layer 750 may be made of the conductive material and thus serve as the bottom electrode.

It is also noted that the term "cantilever" is used in this description in a broad sense to describe a structure that has an anchored end, a resilient portion extending from the anchored end to an exertion end where a spring force is exerted to activate or move the resilient portion. A cantilever thus does not necessarily suggest a literal one-dimensional beam-like cantilever, but also includes similar structures have multi-beams extending in different directions such as a bridge, or a crossbar, and most definitely also includes area or plane springs (two-dimensional "cantilevers") in which the anchored end may be an extended line. The extended anchored end may be a closed perimeter of an area or a portion thereof. The resilient portion may be an extended area. The exertion end may be a single point, a small area, or an extended line (close ended, open-ended, or segmented).

The lower base portion includes a part of a substrate 710 that is shared by multiple cMUT elements of the same cMUT 700. The cavity 730 may be formed directly on the substrate 710 by removing a proper amount of the material of the substrate 710, or formed by adding materials to a surface of the substrate 710. The layer 720 of the upper base portion may be formed using a separate layer placed over the cavity 730.

As shown in FIG. 7, the cMUT elements 701 and 702 are divided from each other by the trench 735 formed through at least the surface plate 770. Preferably, the trench 735 may also cut through the spring layer 750 for further separation. In addition, the trench 735 may have an extension including a lower trench 732 that cuts through the layer 720 and further down into the substrate 710 passing the cavity 730. The lower trench 732 may further improve acoustic decoupling between cMUT elements 701 and 702. Each cMUT element has a variable capacitor element defined by a top electrode and the bottom electrode similar to that in the cMUT element 701, and each cMUT element has a cavity element like the cavity 740 below the variable capacitor element.

The acoustic decoupling features described herein maybe especially useful to the cMUT designs with embedded springs (ESCMUT), an example of which is shown in FIG. 7. Unlike conventional cMUT, in which the acoustic ring and acoustic coupling between cMUT elements goes through the entire substrate, in ESCMUT the acoustic ring and acoustic coupling between cMUT elements generally only goes through the spring anchor 740. As a result, the cavity 730 may be designed to latterly expand only an area directly underneath the spring anchor and not reach far beyond that. In addition, because the trenches 732 can be embedded underneath the cMUT surface plate 770, the fill factor of the transducer is maximized. These features may be especially important for high frequency cMUT arrays.

FIG. 8 shows an exemplary fabrication method to add embedded cavities and trenches in the substrate of a conventional cMUT array.

The first two steps in FIG. 8 are similar to the first two steps described in FIG. 6. A substrate wafer 810 is provided and cavities 830 are formed on the surface of the substrate wafer 810. Subsequently, another wafer is placed over the cavities 830 to form a layer 820 covering the cavities 830.

Figure 83:
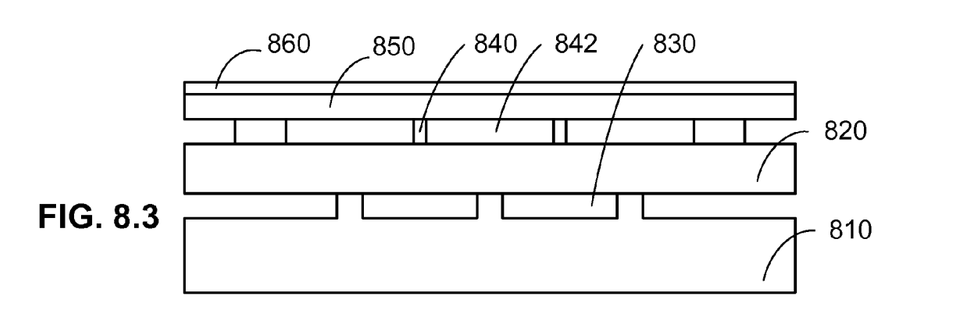

At step 3 (FIG. 8.3), a conventional membrane-based cMUT is fabricated on top of the layer 820. The membrane-based cMUT has a membrane 850 supported by membrane supports 840 and spaced from the layer 820 to define transducing space 842 therebetween. A top electrode 860 is placed over the membrane layer 850. A bottom electrode may either be served by the layer 820 itself if it is conductive, or served by a separate conductive layer (not shown) placed on or embedded in the layer 820.

Figure 84:
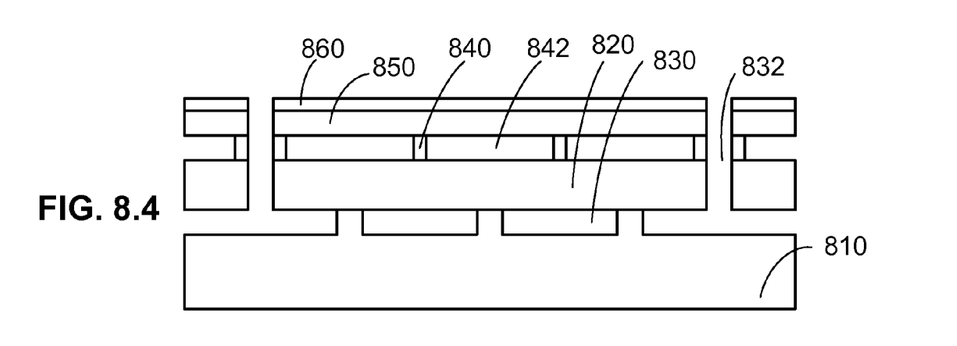
Figure 91:
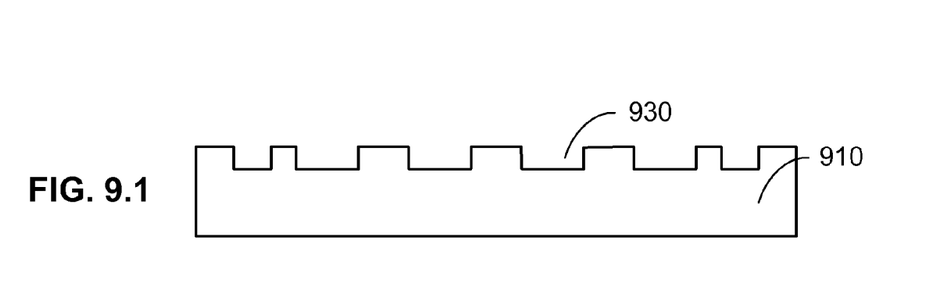
Figure 92:
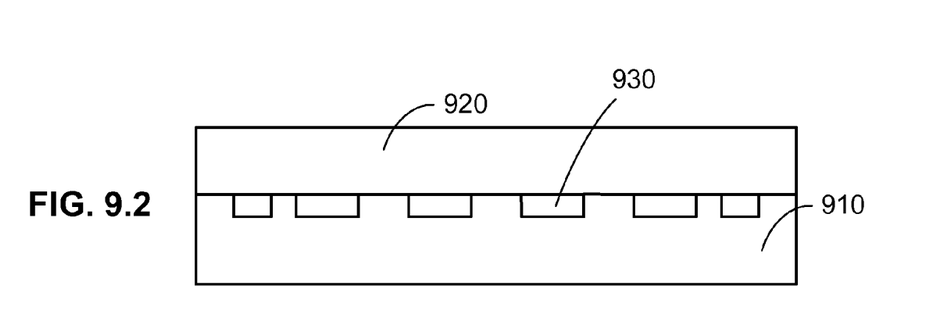

At step 4 (FIG. 8.4), trenches 832 are etched between cMUT elements. The trenches 832 may reach or further go beyond the bottom of the embedded cavities 830 to improve acoustic decoupling.

FIG. 9 shows an exemplary fabrication method to add the embedded cavities and trenches in the substrate of an ESC-MUT array.

The first two steps in FIG. 9 are similar to the first two steps described in FIG. 6 or FIG. 8. A substrate wafer 910 is provided and cavities 930 are formed on the surface of the substrate wafer 910. Subsequently, another wafer is placed over the cavities 930 and forms a layer 920 covering the cavities 930.

Figure 93:
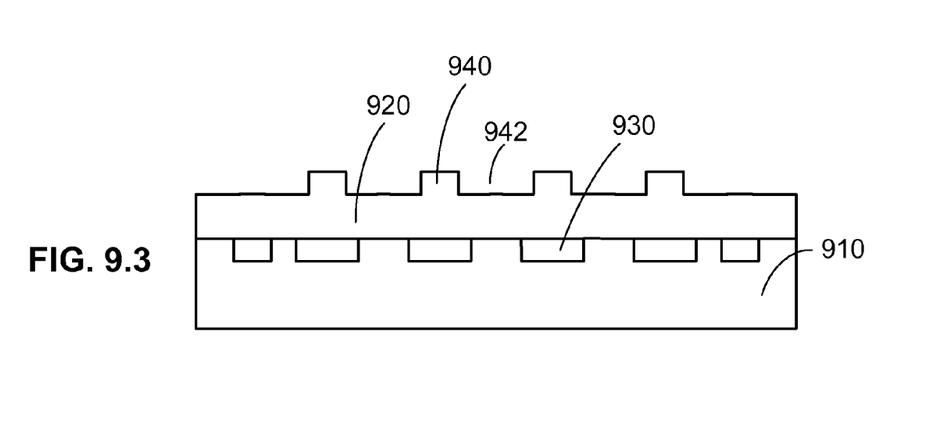

At step 3 (FIG. 9.3), cavities 942 are formed to define spring anchors 940 on the layer 920.

Figure 94:
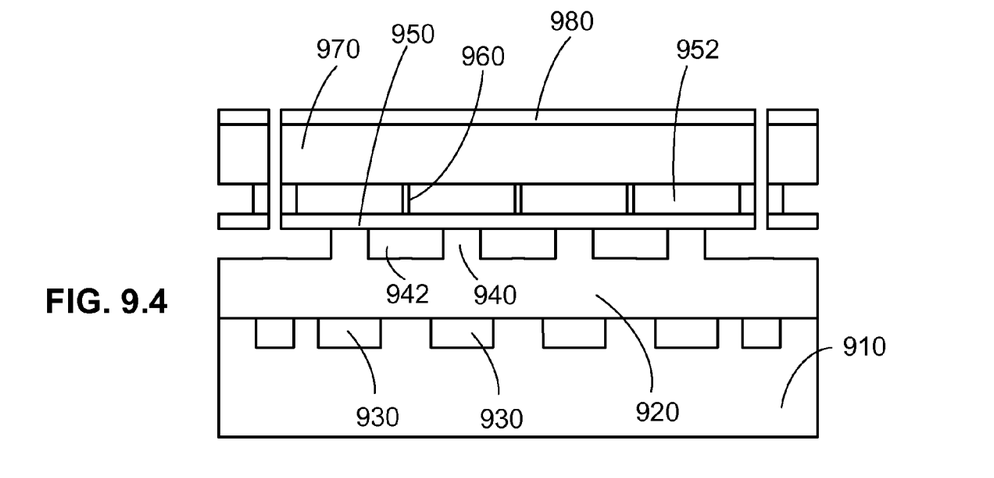

At step 4 (FIG. 9.4), an ESCMUT is fabricated over the cavities 942, the spring anchors 940 and the layer 920. The ESCMUT may be fabricated using any method described in the several patent applications referenced to and incorporated herein. The ESCMUT has a structure similar to that described in FIG. 7. The cMUT is built on layer 920. A spring layer 950 is anchored by spring anchors 940 connected to the layer 920 of the upper base portion. The spring anchors 940 space the spring layer 950 from the layer 920 of the upper base portion to form a cantilever-like structure having an anchored portion and a movable portion. The movable portion of the spring layer 950 is suspended from the layer 920 to form a cantilever. A surface plate 970 is disposed above the spring layer 950 and supported by spring-plate connectors 960 which are connected to a movable portion of the spring layer 950. The spring-plate connectors 960 space the surface plate 970 from the spring layer 950 to define a transducing space 952. The surface plate 970 includes a top electrode 980, which may either be a separate layer or an integral part of the surface plate 970 if the surface plate 970 is made of a conductive material. To make a functional cMUT, a variable capacitor is formed between the top electrode 980 and a bottom electrode, which may be served by any of the spring layer 950, the spring anchor 940 and the layer 920.

Figure 95:
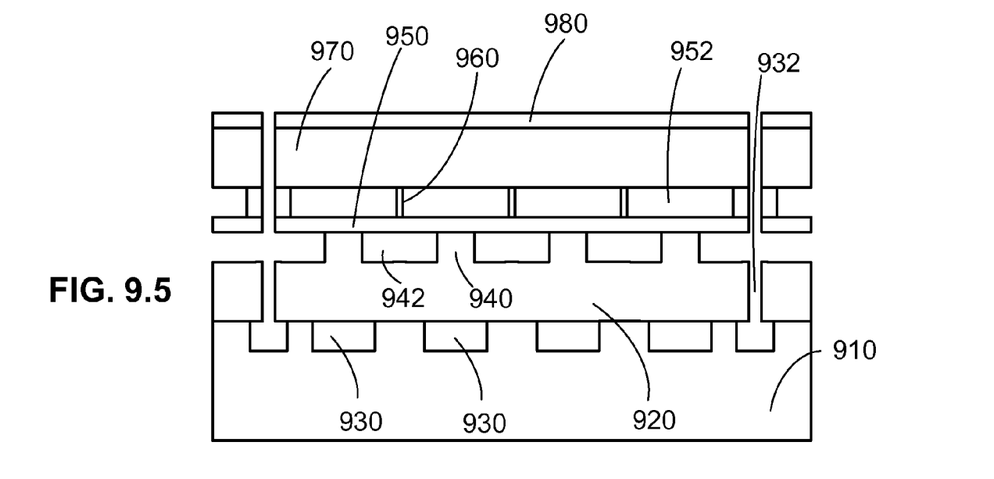

At step 5 (FIG. 9.5), trenches 932 are etched between cMUT elements. The trenches 932 may reach or further go beyond the bottom of the embedded cavities 930 to improve acoustic decoupling.

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. A capacitive micromachined ultrasonic transducer (cMUT), comprising:
   a base having a lower base portion and an upper base portion, the lower base portion and the upper base portion defining a cavity therebetween, the upper base portion having a first electrode; and
   a movable layer disposed above the upper base portion and supported by a support connected to the upper base portion, the support spacing the movable layer from the upper base portion to define a transducing space, the movable layer having a second electrode opposing the first electrode to evacuate a variable capacitor between the base and the movable layer.

2. The cMUT as recited in claim 1, wherein the lower base portion comprises a substrate.

3. The cMUT as recited in claim 1, wherein the cavity is formed on the lower base portion by removing a part of the lower base portion.

4. The cMUT as recited in claim 1, wherein the upper base portion comprises a separate layer placed over the cavity.

5. The cMUT as recited in claim 1, wherein the bottom electrode comprises a separate layer placed over the cavity, the separate layer being electrically conductive.

6. The cMUT as recited in claim 1, wherein the upper base portion comprises a support layer placed over the cavity, the support layer being electrically non-conductive, and wherein the first electrode comprises a conductive layer placed on the support layer.

7. The cMUT as recited in claim 1, wherein the movable layer comprises a membrane, and wherein the second electrode is placed on the membrane.

8. The cMUT as recited in claim 1, wherein the upper base portion has a thickness that is small enough to result in an acoustic ring frequency that is substantially separated from an operating frequency of the cMUT.

9. The cMUT as recited in claim 1, wherein the cMUT is divided by trenches into a plurality of cMUT elements each having a variable capacitor element and a cavity element below the variable capacitor element.

10. The cMUT as recited in claim 9, wherein the cMUT includes a surface plate and a spring layer, and the trenches are formed through the surface plate, the spring layer and the upper base portion.

11. A capacitive micromachined ultrasonic transducer (cMUT), comprising:
    a base having a lower base portion and an upper base portion, the lower base portion and the upper base portion defining a cavity therebetween;
    a spring layer disposed above the upper base portion and anchored by a spring anchor connected to the upper base portion, the spring anchor spacing the spring layer from the upper base portion to form a cantilever-like structure having an anchored portion and a movable portion; and
    a surface plate disposed above the spring layer and supported by a spring-plate connector connected to the movable portion of the spring layer, the spring-plate connector spacing the surface plate from the spring layer to define a transducing space, wherein the surface plate includes a top electrode, and wherein at least one of the spring layer, the spring anchor and the upper base portion includes a bottom electrode opposing the top electrode to evacuate a variable capacitor therebetween.

12. The cMUT as recited in claim 11, wherein the lower base portion comprises a substrate.

13. The cMUT as recited in claim 11, wherein the cavity is formed on the lower base portion by removing a part of the lower base portion.

14. The cMUT as recited in claim 11, wherein the upper base portion comprises a separate layer placed over the cavity.

15. The cMUT as recited in claim 11, wherein the bottom electrode comprises a separate conductive layer which is a part of the spring layer.

16. The cMUT as recited in claim 11, wherein the bottom electrode is an integral part of the spring layer.

17. The cMUT as recited in claim 11, wherein the cMUT is divided by trenches into a plurality of cMUT elements each having a variable capacitor element and a cavity element below the variable capacitor element.

18. The cMUT as recited in claim 17, wherein the trenches are formed through both the surface plate and the spring layer.

19. The cMUT as recited in claim 17, wherein the trenches are formed through the surface plate, the spring layer and the upper base portion.

20. A method for fabricating a capacitive micromachined ultrasonic transducer, the method comprising:
    providing a substrate;
    forming a cavity on a surface of the substrate;
    placing a cover layer over the cavity; and
    completing a cMUT structure on top of the cover layer, wherein the cMUT structure includes a spring layer disposed above the cover layer and a first electrode and a second electrode defining a variable capacitor, at least one of the first electrode and the second electrode being movable to vary the variable capacitor.

21. The method as recited in claim 20, wherein the first electrode resides in or on the cover layer.

22. A method for fabricating a capacitive micromachined ultrasonic transducer, the method comprising:
    providing a substrate;
    forming a cavity on a surface of the substrate;
    placing a cover layer over the cavity;
    forming a spring anchor on the cover layer;
    placing a spring layer over the spring anchor, when placed the spring layer having an anchored portion and a movable portion, the anchored portion being anchored and the spring anchor;
    forming a spring-plate connector on the movable portion of the spring layer; and
    placing a surface plate over the spin-plate connector,
    wherein the cMUT structure includes a first electrode and a second electrode defining a variable capacitor, at least one of the first electrode and the second electrode being movable to vary the variable capacitor.

\* \* \* \* \*